US008652184B2

(12) United States Patent
Bare

(10) Patent No.: US 8,652,184 B2
(45) Date of Patent: Feb. 18, 2014

(54) RESONANT FREQUENCY DEVICE

(76) Inventor: James E. Bare, Albuquerque, NM (US)

( * ) Notice: Subject to any disclaimer, the term of this patent is extended or adjusted under 35 U.S.C. 154(b) by 1069 days.

(21) Appl. No.: 12/461,706

(22) Filed: Aug. 21, 2009

(65) Prior Publication Data
US 2010/0049261 A1 Feb. 25, 2010

Related U.S. Application Data

(60) Provisional application No. 61/136,259, filed on Aug. 22, 2008.

(51) Int. Cl.
*A61N 1/39* (2006.01)
(52) U.S. Cl.
USPC ............. 607/1; 607/2; 607/88; 607/156
(58) Field of Classification Search
USPC ............. 607/1, 60–63; 333/32–35, 337
See application file for complete search history.

(56) References Cited

U.S. PATENT DOCUMENTS

| 5,570,286 | A | * | 10/1996 | Margolis et al. | 701/36 |
| 5,908,441 | A | * | 6/1999 | Bare | 607/1 |
| 6,221,094 | B1 | * | 4/2001 | Bare | 607/1 |
| 6,608,603 | B2 | * | 8/2003 | Alexopoulos et al. | 343/860 |
| 8,269,571 | B2 | * | 9/2012 | Bare | 332/149 |
| 2005/0043000 | A1 | * | 2/2005 | Mitsunaka et al. | 455/314 |
| 2006/0259024 | A1 | * | 11/2006 | Turovskiy et al. | 606/33 |
| 2009/0069671 | A1 | * | 3/2009 | Anderson | 600/424 |

* cited by examiner

*Primary Examiner* — George Manuel
*Assistant Examiner* — Minh Duc Pham
(74) *Attorney, Agent, or Firm* — Welsh Flaxman & Gitler LLC

(57) ABSTRACT

A resonant frequency device provided with a transmitter, an amplifier and an impedance matching circuit connected to an antenna, such as a plasma antenna. A voltage or current balun could be provided between the impedance matching circuit and the antenna.

8 Claims, 6 Drawing Sheets

Device Components With Balun

Device Components Without Balun

Improvement in Pulse Output Shape With Frequency

New Device output at 40 Hz with 50 % Duty Cycle

Old Device Output at 40 Hz with 50% Duty Cycle

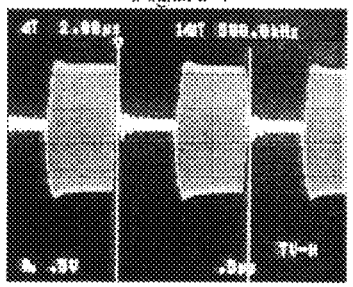
New Device Output at 500 KHz
50% Duty Cycle
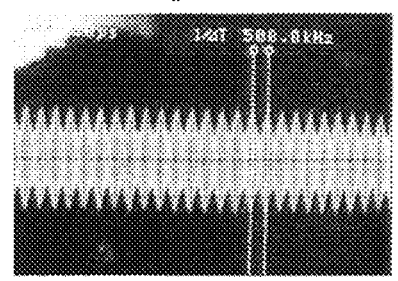
Old Device Output at 500 KHz
With 50% Duty Cycle

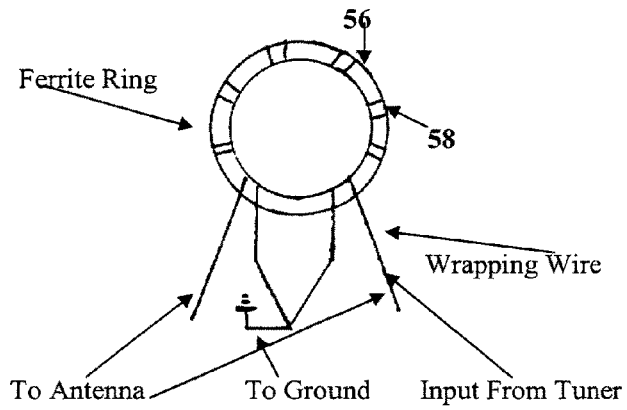
Figure 11
Voltage Balun – Bifilar Wound, Small and Large are identical except for size (diameter) and number of winds of wire
Device Components With Balun
Figure 5
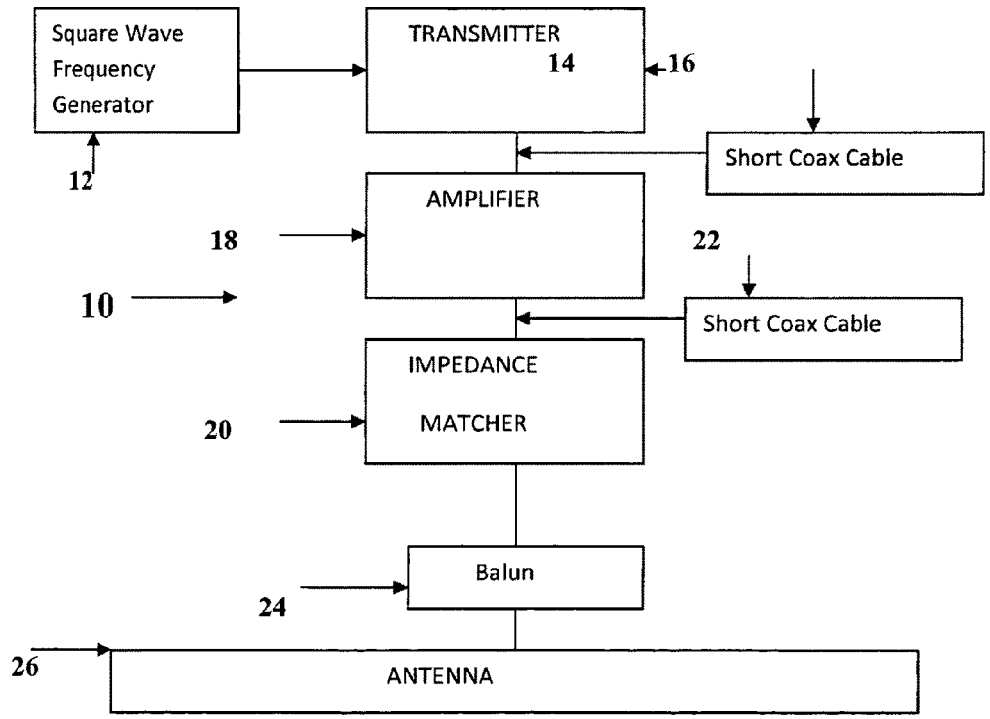

Application to Create Electrokinetic Effects

Tube Capacitive Coupling Method

Internal Electrode Glass Plasma Tubes/Antennas . To Include Lasers and other Gas Filled Light Emission Tubes
Figure 9
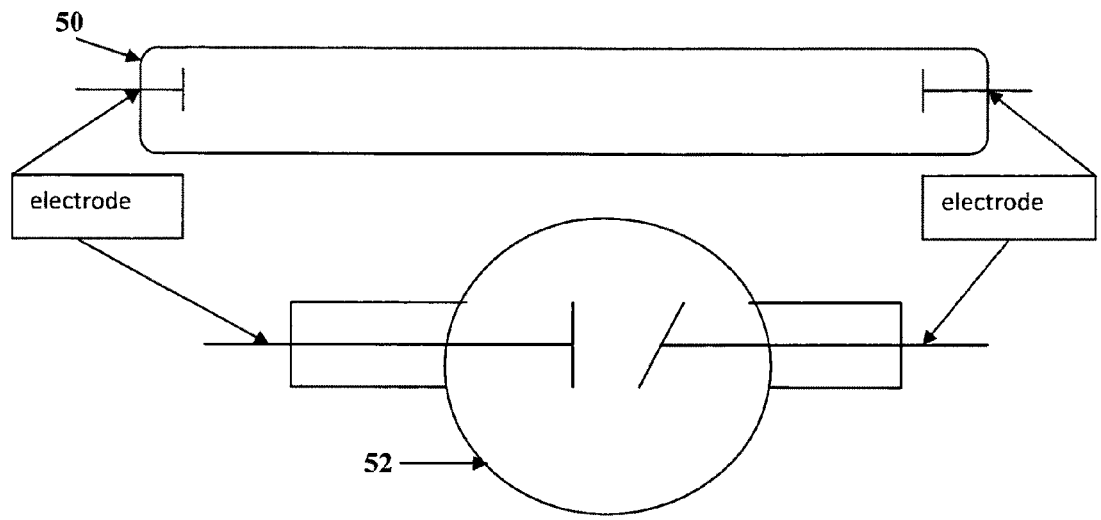
Balun Types
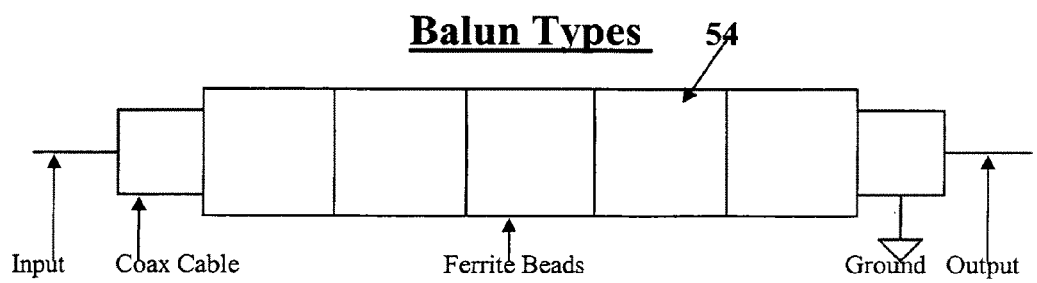
Figure 10
Current Balun

RESONANT FREQUENCY DEVICE

CROSS REFERENCES TO RELATED APPLICATIONS

The present application claims the priority of U.S. provisional patent application Ser. No. 61/136,259, filed Aug. 22, 2008, as well as U.S. patent application Ser. No. 12/457,502, filed Jun. 12, 2009, and are incorporated herein by reference.

FIELD OF THE INVENTION

The present invention is directed to the field of resonant of frequency devices having utility as a therapy device producing bio-physiological effects.

BACKGROUND OF THE INVENTION

The device of the present invention improves all of these operational attributes by a range of many factors via various methods and implements. This improved device utilizes significantly improved components that greatly increase the modulation capability, commercial applications, and creation of biophysiologic effects by factors of several times over the existing device. This new device consists of a frequency generator (preferably square wave), a transmitter, an amplifier, an impedance matcher (antenna tuner), a balun or lack of balun, and an antenna (plasma tube or metallic depending upon application). Design and operation of the Resonant Frequency Therapy device disclosed in U.S. Pat. No. 5,908,441, issued Jun. 1, 1999, and in U.S. Pat. No. 6,221,094, issued Apr. 24, 2001, both entitled "Resonant Frequency Therapy Device" issued to the present inventor show that there are significant limitations and capabilities of the components utilized in their construction. The patented devices are based upon utilization of a transmitter derived from that of a CB radio. All components attached to such transmitter have inherent limitations that ultimately limit the ability of the device to produce bio physiologic effects including the treatment of infections, disease states and cancer, and it's applicability to data transmission, and radar. The major limitations involve the rise and fall time of the pulse envelope, the frequency modulation capability of the amplifier, and the ability to manipulate the modulation frequency. The transmitter utilized in the prior art patents is limited to about one micro second rise and fall time.

Due to the use of a modulation transformer there is limitation to the modulation frequency handling capability of the transmitter. Another limitation on modulation frequency with existing transmitters is the use of an audio amplifier to step up the input audio signal voltage and current to the modulation transformer. Existing audio amplifiers for this purpose are limited to about 400,000 Hz. Existing transmitters, due to limitation of the modulation transformer and the audio amplifier, are limited to about 300,000 Hz maximum modulation frequency, and this is achieved only with a significant degradation of the pulse envelope.

The presence of a modulation transformer also severely disrupts the pulse envelope with modulation frequencies below 100 Hz. Simply connecting a transmitter with faster rise and fall times to components is found in U.S. Pat. Nos. 5,908,441 and 6,221,094, does not mean that the output pulse delivered from the antenna of the device will show improvement. Each component downstream from the transmitter must be equally as capable of the transmitter in handling, and thus not distorting or diminishing the quality of the oscillating electrical pulse.

The transmitter utilized in the existing patents is limited to about 1 micro second rise and fall times. This new device utilizes a new transmitter revealed in U.S. patent application Ser. No. 12/457,502, filed Jun. 12, 2009, which is incorporated by reference. This new transmitter and its attached components that make up the improved Frequency Therapy Device—(amplifier, tuner, plasma tube (or other antenna type) is capable of producing rise and fall times of approximately 40 nanoseconds. The improvement of rise and fall times alone is that of about 25 times over the existing device. The existing device, as mentioned in these patents, utilizes a large ferrite balun in the antenna tuner. It has been found that a large ferrite balun causes a limitation of both modulation frequency response, and limitation of the rise and fall times of the pulse envelope. For example, the large balun used with existing devices, will severely distort the pulse envelope limiting rise and fall times of the pulse envelope to approximately 1 microsecond and the modulation pass band to approximately 500 KHz.

The existing devices described in U.S. Pat. Nos. 5,090,441 and 6,221,094 utilize long lengths of coaxial cable between the components. It has been found that at high modulation frequencies, these lengths of coaxial cable can severely degrade the pulse envelope and diminish the modulation frequency pass band.

Additionally, the prior art patents to the present inventor are limited to pulses longer than 1 microsecond and are incapable of many bio-physiological effects. Pulses of less than 1 microsecond durations will selectively charge the internal organelles and internal membranes of a cell, and not change the outer plasma membrane. Thus the prior art patents will charge the external cells membrane (plasma membrane) simultaneously with internal organelles and internal organelle membrane. There is no selectivity with these devices.

SUMMARY OF THE INVENTION

The deficiencies of the prior art are addressed by the present invention which utilizes a new transmitter and its attached components that make up the improved frequency therapy device. These components include an amplifier, a tuner, a plasma tube or other antenna type which is capable of rise and fall times of approximately 40 nanoseconds. This is approximately 25 times greater than the rise and fall times of the aforementioned existing devices. The new transmitter of the present invention and its attached accessory components (amplifier, tuner and antenna) are capable of outputting frequencies as high as 4 MHz with minimal degradation of the pulse envelope. This frequency range is improvement of approximately 13 times over the existing devices.

The present invention describes a device to be used in radar, data transmission, and the production of bio-physiologic effects. These effects have been found capable of affecting multicellular organisms, and micro organisms including all members of the 5 Kingdoms i.e., Fungi, Monera, Animalia, Plantae, and Protista. Effects extend to all viruses, prions, other infective "agents" and all cell types including cancer. The emissions can influence the nervous system of those organisms that should possess such and create pain relief, sedation and other influences on nerves of both the peripheral and central nervous systems. The device can be utilized for the treatment of infections and various disease states including cancer, the enhancement of ionizing radiation effects on the body, the enhancement of bioactive compounds on the body such as chemotherapeutic medications and antibiotics, and manipulation of genetic expression.

Since the presence of a prior art modulation transformer can severely disrupt the pulse envelope with modulation frequencies below 100 Hz, the transmitter of the present invention would produce a highly consistent and properly shaped pulse form that range from less than 1 Hz to beyond 3 MHz. FIG. 1 shows the prior art device with an output at 40 Hz with a 50% duty cycle. This should be compared to the output illustrated in FIG. 2 having a square wave output at 40 Hz with a 50% duty cycle. FIG. 3 illustrates a prior art device with an output at 500 KHz with a 50% duty cycle and is compared to the output of the present invention as shown in FIG. 4 at 500 KHz at a 50% duty cycle.

The modulation transformer and the audio amplifier also create limitations of the ability to fully adjust the duty cycle of the modulation signal. Extremely high square wave duty cycles (greater than 70%) tend to overheat both the modulation transformer and the audio amplifier and cause failure of the modulation transformer and the audio amplifier. The present invention shows significant improvement with modulation frequency duty cycles from 1% to over 99%. In order to obtain the maximum utilization of the improved devices capabilities, it is necessary to modulate the new transmitter with a square wave generator that can generate square waves with rise and fall times shorter than that of the prior art devices capabilities, i.e. less than 40 nanoseconds. These square wave generated outputs are illustrated in FIGS. 2 and 4.

The present invention utilizes various configurations. Three of these configurations utilize a balun which is of a lesser size than included in the devices described in U.S. Pat. Nos. 5,908,441 and 6,221,094. Another configuration operates without the benefit of a balun. The elimination of the ferrite balun would produce the best output frequency range and pulse shape but would make plasma initiating difficult with an antenna so designed. In yet another configuration, a small voltage type balun is utilized to step up the output voltage of the transmitter and ease plasma initiation. Due to the severe overheating effects, this small voltage round balun is only useable with lower power amplifiers generally under 150 watts. The large ferrite voltage balun as described in U.S. Pat. Nos. 5,908,441 and 6,221,094, when combined with other component improvements of the present invention can produce rise and fall times of the pulse envelope of 330 nanoseconds, a three fold improvement over the capabilities of these existing devices. A current balun can also be used in one of the configurations which offer a superior pulse shape through and modulation frequency pass band to that of the voltage balun. The current balun and the large voltage balun can handle very high amplifier power levels, far in excess of 150 watts.

The improved device utilizes an impedance matcher (antenna tuner). Different shapes and types of plasma tubes, different tube gasses, different gas volumes, different gas pressures, different metallic antennas and other output devices such as a laser or a pair of electrodes for use in creating electro kinetic effects all have different impedances. These impedances must be matched between the amplifier and the antenna. Failure to match impedances will result in diminished effectiveness of the device, or destruction of the amplifier. For a plasma tube, there are two primary impedances, the impedance of the tube without a plasma, and the impedance of the tube once a plasma is created. It is almost impossible to start a plasma tube without having some sort of adjustable impedance matching circuit between the amplifier and the plasma antenna. Due to the presence of many harmonics and the creation of sidebands produced at MHz modulation frequencies, the construction of the tuning capacitors within the antenna tuner (impedance matching circuit) are critical to pass band and output pulse shape of the matching circuit. Ideally the matching circuit would be designed to be almost self resonant using an inductor coil and minimal adjustable capacitance. What has been found is that relatively large size tuning plates in the air capacitors are superior in tuning ability, pass band, and maintenance of pulse shape, to those of small tuning plates. As an example, a small tuning plate might be ¾ inch in diameter and have a surface area of around 1 square inch. A large tuning plate might be 2 inches or more in diameter and have a surface area of over 6 square inches. A large number of tuning plates—will cause limitation of the modulation (pulse) frequency pass band. The ideal capacitor for use in not causing distortion of the pulse envelope and allowing for a maximum modulation frequency pass band will have a relatively large surface area to the plates, and only 3-5 plates to compose the capacitor.

The present invention would utilize coaxial cables that are as short as possible or are a direct connection between the components such as integrated "all on one circuit board" configuration comprising the entire electrical system which are also the best management of the oscillating pulse signal with minimum distortion. The length of this short coaxial cable should be less than one foot.

The antenna used for the output of this improved device needs to be attached closely to the impedance matching circuit. Use of long cables or wires to connect to the antenna will not only degrade the signal, but will limit the modulation frequency pass band. The antenna construction must be designed to account for the modulation frequency bandwidth and the integrity of the pulse envelope. Due to the formation of side bands, and harmonics generated by the pulse transmitter and the amplifier, a metal antenna might be required to pass a bandwidth of frequencies that extend across a bandwidth exceeding 8 MHz or more from the transmitter's carrier frequency. This is due to sideband formation and the existence of harmonics. If utilizing a plasma type antenna there are two basic design choices. One design choice would be an antenna with internal electrodes. A second design choice would not include internal electrodes in the antenna. Internal electrode tubes with close approximation (1 to 2 inches for example) such as described in the existing device as mentioned in U.S. Pat. Nos. 5,908,441 and 6,221,094, are ideal for wide band width modulation frequency response, and minimal rise and fall times of the pulse envelope.

Long tubes with no internal electrodes such as one might utilize in a plasma tube or laser, are capacitively coupled to the output of the impedance matching circuit. To minimize rise and fall times and increase modulation frequency response it is necessary to utilize an insulating material of high dielectric value, high temperature resistance and high breakdown voltage resistance between the tube and the output wires of the impedance matcher. Capacitive coupling between the impedance matcher and tube is in usage with the existing devices as described in U.S. Pat. Nos. 5,908,441 and 6,221,094 but what has been found is that the use of a high dielectric constant and high breakdown voltage resistance material is mandatory when using capacitive coupling methods at high modulation frequencies. The dielectric material will increase modulation frequency response and pulse envelope shape as emitted from the plasma tube. An advantage of using capacitive coupling with a high dielectric insulator to excite the tube is that one may use much higher power levels without danger of overheating of electrodes or possible melting of the glass around the electrodes and sacrificing tube integrity. When using insulating materials a problem with RC times ensues. There is an inherent resistivity within the plasma tube that is higher when the plasma is not present, than when the plasma is present and conducting current. The addition of a dielectric material to the tube, as an insulation between the wires connecting the tube to the impedance matcher as a wrapping, will add capacitance to the system and thus influence RC discharge times. Care must be taken that the amount of dielectric material is small and the coupling area of the tube to the impedance matcher is small. A material with an excessive high dielectric property, or a tube coupling that is composed of a large surface area of dielectric material and a large coupling surface area to the tube such as a copper collar, can create enough capacitance to diminish the frequency output capability of the plasma tube. Excessively large coupling areas will also affect the quality of the created pulse envelope and slow rise and fall times. One ideal insulator material is Teflon. Teflon has a dielectric constant of roughly 2, but also possesses a very high voltage breakdown resistance and high heat tolerance.

The presence of a modulation transformer also severely disrupts the pulse envelope with modulation frequencies below 100 Hz. See pictures below—The new equipment and transmitter produce a highly consistent and properly shaped pulse from <1 Hz to beyond 3 MHz. The modulation transformer and audio amplifier also create limitations of the ability to fully adjust the duty cycle of the modulation signal. Extremely high square wave duty cycles (>70%) tend to overheat both the modulation transformer and audio amplifier and cause failure of said modulation transformer and audio amplifier. This new equipment shows significant improvement with modulation frequency duty cycles from 1% to over 99%.

In order to obtain the maximum utilization of the improved devices capabilities it is necessary to modulate the new transmitter with a square wave generator that can generate square waves with rise and falls times shorter than that of devices capabilities i.e. less than 40 ns.

The gas type and pressure utilized in plasma tube antennas with this improved device is critical to obtain optimal modulation frequency capability and pulse shape integrity. The input to the tube being a pulse causes the tube plasma to pulse off an on. It has been found that a highly conductive gas such as neon will at a certain point continue to stay lit between pulses and cause a degradation of the pulse envelope and the output modulation frequency response. A highly resistive gas such as helium, especially when used at pressures 20 mm and above will tend to "self quench" between pulses and offers a very wide modulation frequency response and minor pulse envelope degradation.

Optimal pulse shape and modulation frequency response (pass band) must be accounted for in the design of the transmitter, any amplifier, impedance matching circuit, or any antenna that comprises it.

A square wave frequency generator with rise and fall times shorter than those the transmitter is capable of generating (40 ns or better) is used to drive a transmitter capable of MHz range of pulse repetition rate (PRR) output. The output from the transmitter is fed to an amplifier that is capable of amplifying the MHz PRR pulses from the transmitter and the amplifier has electrical components capable of handling the instantaneous high voltages created by short pulses of fast rise and fall times of MHz PRR. Output from the amplifier is fed to an impedance matcher circuit with tuning capacitors of large surface area tuning plates, but small number of plates. Output from the impedance matcher is then fed to either a metallic antenna tuned to manage the MHz PRR or to a plasma antenna. The Plasma antenna has gasses such as helium and gas pressures capable of outputting MHz PRR.

Due to the diminished rise and fall times of the pulse envelope, the improved duty cycle manipulation, and frequency range of this improved frequency device, biophysiologic effects are significantly improved over the existing device.

Biophysiological effects are improved when the output of the transmitter is fed to an antenna. Regardless of whether the antenna is a conventional design, or a plasma tube, the emitted EM waves will have a directional vector which will intersect with any object nearby. Should that object be conductive, it can be considered to have the electrical property of inductance. The output of the transmitter being a pulse, means that all EM energy is contained within the pulse, and thus a conductive object is subject to Faraday's Law of Induction in a unique manner.

Faraday's law states—"The magnitude of an electromagnetic force induced in a conductor is proportional to the rate of change of the magnetic flux that cuts across the conductor."

Mathematically, Faraday's law is written as:

$$E=-(DF/Dt)$$

where E is the induced electromotive force in volts, DF is the change in magnetic force in webers (a Weber is equal to 1 volt—second), and Dt is the amount of time in seconds in which the change in magnetic force takes place.

From the above formula we see that the amount of induced voltage induced in the conductor is determined by the amount of magnetic flux and the rate at which the magnetic field lines cut across the conductor.

The greater the number of magnetic field lines cutting across a conductor, the greater the induced voltage. Additionally, the faster the magnetic field lines cut across a conductor, or the conductor cuts across the magnetic field lines, the greater the induced voltage.

Should the magnetic flux generated by transmitted pulse cut across any electrically conductive object, the induced voltage in that object will conform to Faraday's law. An RF wave contains both an electrical and magnetic component. In the circuit utilized for this or the existing transmitter as described in U.S. Pat. Nos. 5,908,441 and 6,221,094, changes in the magnetic flux component would be minimal. One could increase the magnetic flux component by simply increasing power output of the device by utilizing further amplification stages or the addition of an external amplifier. One could also utilize an antenna designed to enhance magnetic flux output. Regardless, changes in the magnetic flux component strength, while important, are limited. It would be very difficult for example, to increase the transmitted magnetic flux field by a factor of 100 times.

Significant changes in the EMF generated within a conductor can be accomplished by simply changing the modulation frequency. The output of the transmitter creates a pulse rate equal to the modulation frequency, and thus, with each transmitted pulse, a magnetic field is generated of a specific time duration. Although the magnetic flux may hold static for a particular antenna, a change in the pulse modulation rate of the transmitter will cause changes in the induced voltage present in any conductor cut by the antennas emitted field. It is simple to change the pulse rate by a factor of 1000 or more times. Thus, in this improved device and the predicate device, the generated electromotive force in any conductor cut by the emitted pulsed magnetic field is predominantly time domain dependent. The induced voltage in a conductor by the output pulse can be extremely large. For example, the improved device by changing from a pulse rate of 300 Hz with a fixed magnetic field strength, to 3 MHz with the same magnetic field strength, a conductor will see an instantaneous induced EMF change of ten thousand times. The existing device, due to limitations of the components could produce a shift from 300 Hz to 300 KHz a change in EMF of only 1000 times. The significantly higher instantaneous EMF has considerable application to the creation of biophysiological effects. It is well known in the literature that large voltages, when applied as short pulses can create many biophysiologic effects such as electroporation and apoptosis.

The present invention offers an improved method of increasing the induced EMF in a conductor of biological or non biological origin by varying its modulation frequency. A similar effect of significant instantaneous induced EMF change can be created by gating the output of the transmitter. One could take a 2 MHz signal and gate it at 4 Hz. Bursts of 2 MHz PRR signal would thus occur 4 times a second. By creating what might be considered as a relaxation time between each signal burst, the conductor would have time to lose any accumulated charge and thus be subject to a maximum induced voltage from the pulse burst. Ideally the charge on the conductor would be allowed to drop to 0 and then be subject to a maximum generated EMF via Faraday's Law.

The device according to the present invention offers an improved method of increasing the induced EMF in a conductor of biological or non biological origin by utilizing a variable gate frequency of the modulation frequency. Such an effect can be seen on an oscilloscope when the improved device is driving a closed tube in which a gas plasma is formed by the RF pulse. As each gated train of pulses is generated, and each gated train of pulses is cut off, a large instantaneous voltage spike can be seen at the leading and trailing end of each pulse within the train of pulses created by the gate frequency. The generated instantaneous voltage spike on each pulse can be of very short time duration. For example at a 10 KHz PRR, the trailing edge voltage spike has been measured at less than 100 ns time duration, with a fall time of under 20 nanoseconds.

"Faraday's Law" has significant interaction with the components of the circuit. This includes components utilized by any amplifier, or antenna connected to the transmitter. A non obvious effect of the generated pulse within the circuit of this transmitter is an increase in the circuit voltages of the transmitter with increases in modulation frequency. Component parts of the device must account for this voltage variation with frequency.

The device according to the present invention will create significant voltages at high modulation frequencies that must be accounted for in component selection of the transmitter, any amplifier, or any antenna connected to it. The transmitter may be utilized with an amplifier which may range up to many thousands of watts of power. The transmitter may be utilized with amplifiers of unlimited power levels to increase the electromagnetic field (EMF) for the production of bio-effects. If using a dipole like antenna, spacing the antenna elements closely together can achieve field strengths sufficient to create many commonly known physiologic effects. By placing a living organism of some sort close to the focal point of the field between the closely aligned antenna elements, one can optimize the physiologic effects. There are many well known bio-physiologic effects mentioned in the literature from the application of high intensity pulsed fields to cells and micro organisms. This can include but are not limited to; sterilization, electroporation, apoptosis, necrosis, transfection, and gene manipulation.

The device of the present invention can be utilized to create sterilization, electroporation, apoptosis, necrosis, transfection, and gene manipulation. Typically such physiologic effects have been accomplished with pulse durations of millisecond to microsecond duration. Recent research has shown that many cellular physiologic effects can be achieved by the use of high power pulses of nanosecond duration. The existing device, as described in U.S. Pat. Nos. 5,908,441 and 6,221,094 being limited to pulses longer than 1 microsecond is incapable of many bio-physiologic effects. Pulses of less than one micro second duration will selectively charge the internal organelles and internal membranes of a cell, and not charge the outer plasma membrane and thus the existing device will charge the external cell membrane (plasma membrane) simultaneously with the internal organelles and internal organelle membranes. There is no selectivity with the existing device. The improved device which is capable of generating sub microsecond pulses is capable of charging just the internal organelles and membranes of a cell, leaving the outer plasma membrane uncharged. Another advantage of the device is that instead of only a few nanosecond pulses per second being generated as in most instruments utilized for this purpose, the device can generate millions of sub-microsecond duration pulses per second.

The device of the present invention can be utilized to create sub-microsecond duration pulses to selectively charge and influence the internal organelles and membranes of a cell without charging the outer plasma membrane. Cellular membranes possess the ability to demodulate amplitude modulated radio transmissions. This means that the demodulated electrical signal forms local to the point of demodulation within the cell membranes. Further, many cell membranes possess the ability to amplify pulsed electrical signals. The demodulated signal thus has the ability to influence the bio-electrochemistry of a cell's outer membranes, and indirectly influence the metabolism of the cell which is dependent upon the outer membranes bioelectrochemistry. Thus, simply by changing the modulation frequency and/or pulse duty cycle of this improved device in order to create sub microsecond pulses, one can selectively create charges on a cell as whole, or on just the interior organelles and membranes of a cell.

The improved transmitter/device being of the AM type and more specifically an overmodulated AM type, allows for demodulation of the side band signals occur in a cell's various membranes. The demodulated signal, a pulsed electrical signal, will affect the bio electrochemistry of the membrane and thus affect the cells physiology.

The well known electrokinetic effect of Electrokinetic Sonic Amplitude (ESA) can be utilized to create a compressional type wave within a cell or living organism's body. ESA occurs when an alternating electrical current is applied to a suspension of charged particles. The particles move back and forth in the liquid in response to the electrical field creating tiny pressure disturbances around the particles in the liquid. If there is a density difference between the particles and the liquid, a macroscopic acoustic wave develops at the boundaries of the suspension.

If a pulse emitted from the device is demodulated within a cell or body, it may produce a compressional type of wave. This wave will travel through the body at an average of 1440 Meters per second, but will vary depending upon the tissue density and other well known attributes of body tissue response to compressional waves.

With this improved device, one must account for the duty cycle of the generated EM pulse in order to determine the width of the generated compressional pulse (wave). Changes in the duty cycle changes the time duration of each EM pulse emitted from the device, creating different pulse widths for a fixed frequency. By knowing the time duration of a single EM pulse, one can calculate the amount of space or distance that each compressional pulse (wave) will occupy. An EM pulse of 500 KHz with a 50% duty cycle will have a time duration of one microsecond. Thus a single compressional pulse of 1 microsecond will occupy 1.440e+6 mm/sec/1e-6 sec=1.440 mm (0.0566 inch). By adjusting either the modulation frequency or the duty cycle, a compressional pulse (wave) generated by a 100 nanosecond duration pulse being generated at a 500 KHz rate (5% duty cycle), would have a dimension of 0.1440 mm. (0.00566 inch).

The device is capable of forming compressional pulses (waves) within a cell or large organism's body. The PRR of the compressional wave is equal to the modulation frequency of the device. The device due its wide modulation bandwidth is capable of generating compressional waves that extend well into the ultrasonic region. The wavelength of the generated compressional pulse (wave) is related both the PRR and the duty cycle of the EM pulse that creates the compressional wave.

A well known electrokinetic effect is that an electrical signal arises when an acoustic wave is applied to a suspension of colloidal particles in an electrolyte solution. The electrical signal is known as the Colloid Vibration Potential (CVP). This has applicability to many different cells and tissues of the body which are filled with many different colloidal like particles and electrolytes. Thus, the CVP will create an increased electrical charge that can create biophysiological effects. For example one of these bio-physiological effects can be Voltage Dependent Ion Gating (VDIG) in which ion channels in many different types of cells can be opened by the presence of an external electrical field. The improved device being capable of MHz modulation levels, improves the ability to manipulate cells using CVP and VDIG.

As a transverse or longitudinal compression wave passes through a cell or tissue, it will have an amplitude. The amplitude of the wave represents the maximum displacement of the individual particles from their previous equilibrium positions. The energy carried by the wave is proportional to the square of its amplitude. Mathematically this is expressed in the equation:

$$E\mu \infty A^2$$

where $E\mu$ is the energy of the wave, and A is the amplitude of the wave. As the transverse or longitudinal wave passes through a cell or tissues, its power (energy) may be absorbed. The amount of power available to be absorbed from the wave is proportional to the square of its amplitude multiplied by its velocity. Since the velocity of conduction remains essentially static inside a cell or tissue, the initial amplitude of the wave (which is based upon the rise and fall time of the pulse envelope and the power of the device) is the primary determinant of the wave's ability to create physiologic effects. The power delivered by the wave if it is absorbed, is proportional to the square of its amplitude times its speed. This is defined mathematically by the equation $P\mu \infty A^2 V$. The speed of the wave is defined as its conduction velocity, which in the body for a compressional wave an average of 1440 M/Sec. The speed being fixed, modest increases in the wave's amplitude can result in significant increases in the power delivered by the wave. The improved device with it's much improved pulse rise and fall times will produce a wave with significantly higher amplitude than the predicate device all other attributes (power, frequency, etc.) being equal.

If a pulse emitted from the device should be demodulated within a conductive media, and then travel through that media as a compressional wave, the opportunity for constructive interference of the pulse exists. If the end point of the conductive media is loosely coupled, the wave when it reaches the end of the media will bounce and return towards its source, creating constructive interference and thus significant high voltage standing waves can be generated within the conductive media. When an object is vibrating at its fundamental frequency, then all the particles that make up the object oscillate in phase with that fundamental frequency. At its natural frequency of oscillation, a standing wave is created within an object. The application of an in phase driving force with the same frequency as the fundamental to the object can very efficiently pump energy into the object via the process of resonance. At resonance, the amplitude of the standing wave within the object increases essentially without limit, until the structure is damaged. The improved device due to increased wave amplitude ability is more effective at creating resonance than the predicate device.

The ability of the improved device to produce high voltage potentials through constructive wave interference, electrokinetic effects, demodulation, amplification, and Faraday's law of induction means that the output pulse can be used for biological manipulation of various physiologic mechanisms within living organisms that is superior to the predicate device. It is known in the literature that changes in the modulation frequency and pulse duration are important to the creation of bio-physiologic effects.

Two separate modulating frequencies when input to the device can be used to create beats. The beat frequency generated is equal to the difference between the two modulating frequencies. If the output of the device is used to create a gas plasma, laser, or other light emitting device, the beat frequency (if below 30 Hz) can be visualized in the plasma. The improved device being capable of MHz modulation levels can create beat frequency effects using two separate frequencies far in excess of the capabilities of the predicate device. For example by using 600,000 Hz and 600,004 Hz one could create a beat frequency of 4 Hz. The predicate device is incapable of creating this effect within these frequency ranges.

The device of the present invention can be used to create beat frequencies within an object that absorbs and demodulates the wave, and within a gas plasma, laser, or other light emitting device excited by the device. The importance of short duration pulses created by two or more modulating frequencies is important to the creation of standing waves. If one inputs two or more different frequencies of identical phases and identical amplitude, to the device and then applies the output signals of the device to a cell, or organism, one will produce standing waves in the cells or organism. Ideally there should be one low frequency (a fundamental) and all other modulating frequencies are a higher harmonic (multiple) of the fundamental. Standing waves will be formed whose amplitude is based upon the vector sum of the frequencies. The summation will create a wave like pattern with an ascending slope and a descending slope. The angle (sharpness) of the slope is dependent upon the frequencies of the waves. Vector summation of the waves is based upon the effects of the demodulated signals at the cellular level which is a consequence of side band formation. When signals within the sidebands generated by different modulating frequencies have identical phases and are also related harmonically, a vector summation will occur thus dramatically increasing the ability of the transmitted wave to create bio-physiologic effects.

The device of the present invention can be used to produce standing waves with cells and organisms. Additionally, this device when modulated by different frequencies that are harmonically related, will produce sidebands that can vectoraly sum via identical phases and will create or increase bio-physiological effects.

Improved dielectrophoretic effects can be produced by the device. All particles exhibit dielectrophoretic activity in the presence of electric fields. Dielectrophoretic (DEP) effects can be used for separation of cells, and other particles. Dielectrophoretic effects are frequency specific for different organisms and substances based upon their dielectric properties. Frequency specificity can be used for separation and identification of different species of bacteria, viruses, fungi, molds, and other living organism's. The use of multiple frequencies to induce dielectrophoretic effects is superior to single frequency DEP in the manipulation of cells, micro organisms and particles. Frequencies utilized in DEP can be from less than 1 Hz to over 1 MHz. The predicate device, being limited to 300 KHz limits the ability to evaluate DEP. The improved device having PRR's beyond 1 MHz allows for full evaluation capability of DEP.

The device can be used to create single and multi frequency dielectrophoretic effects (MFDEP). The device can be used to create DEP or Multi Frequency DEP via the combined mechanism of the frequency of the carrier wave, the modulation frequency, the gate frequency, and the addition of one of more frequencies.

The improved device can create physiologically active bio photons of specific wavelengths within single cells, and multicellular organisms of shorter wavelength than those of the predicate device. Published papers on the existing device show the wavelength of the biophotons created are directly related to the modulation frequency. Increases in modulation frequency can produce shorter wavelength biophotons. The existing device being limited to about 300 KHz is capable of producing biophotons with wavelengths in the near ultraviolet regions of approximately 380 nmk. This improved device being capable of multi MHz levels of modulation can create Biophotons with high energy levels, around 250 nm or less. The higher energy (shorter wavelength) Biophotons being in the Ultra Violet range produced by this improved device can have very pronounced biophysiologic effects upon cells.

It is known in the literature that DNA transfection can be accomplished using low amplitude low frequency AC fields with oscillation rates of from 0.1 to greater than 1 MHz. This improved device having a PRR beyond the 300 KHz limit of the predicate device can be used to create superior DNA transfection effects. The device can be used for DNA transfection of bacteria utilizing frequencies from less than 1 Hz to more than 1 MHz.

The device can produce electro-osmosis and electroendocytosis effects. Via electro osmosis and electro endocytosis methods one may influence the flow of ions into and out of a cell or micro organism. Published literatures show that when a pulsed EM field is combined with cancer chemotherapy medication or antibiotics it is possible to enhance the effectiveness of the medications. For antibiotics this is known as the "Bioelectric Antibiotic Effect". The devices effects are not just limited to these types of medications, but other existing medications and new medications can be designed to work specifically with the pulsed EM field created by the device. Due to the variability of the pulse duration effects of the device on cells, one could selectively affect either the entire cell or just the interior of the cell and thus control to some degree how that cell interacts with the applied medication.

It is known in the literature that a molecule that is immobilized or is tumbling more slowly than the frequency of an oscillating electric field, may interact with the field to produce chemical effects. This interaction can increase the rate of chemical reactions and include the exchange of energy between the field and the conformation of the molecule. The molecule can absorb and couple energy of the field to drive endergonic and exergonic reactions. That is, the energy within extremely high ECC fields can be used to transduce electrical energy into chemical energy, and chemical energy into electrical energy. Key to understanding ECC is that the efficiency of the coupling between the molecule and the oscillating electrical field depends upon the field strength and the frequency of the field. The improved device having the ability to increase field strengths and PRR's beyond that of the predicate device can create superior ECC effects to that of the predicate device. Via production of ECC by the device, it is possible to change the conformation of various proteins. Many proteins are toxic (poisonous), for example Prions, bacterial exotoxins and mold exotoxins. Changing the conformation of a protein will disable the ability of the protein to be physiologically active and thus inactivate any toxic effects of said protein Polar molecules emit electromagnetic energy due to internal vibrational states. Such polar oscillators can absorb electromagnetic energy and their reactions to the external field can vary based upon the frequency of the field. For example microtubules are electrically polar and will react to an oscillating external field to transport molecules and charges. Micro tubules have been shown to be sensitive to frequencies within the GHz ranges. Recent testing of the improved device demonstrates that due to mixing effects within a plasma tube antenna, near field emissions extending up to 14 GHz have been noted.

Published literature shows that cellular plasma membranes can demodulate pulsed electromagnetic fields. An electrical signal will form local to the point of demodulation. This electrical signal will increase the electropotential of the plasma membrane. VDIG, electro—osmosis, electro-endocytosis, and other bio physiologic effects can be possible via demodulation of the device's pulsed EMF. The significance of raising the electrical potential of plasma membranes is considerable. Non dividing cells have large transmembrane potentials (TMP). It is known that cancer cells have very low transmembrane potentials—published papers demonstrate that increasing the transmembrane potentials of cancer cells will slow their rate of replication and affect many other aspects of cancer cell metabolism. High cellular plasma transmembrane potential can be utilized to thwart infection by viruses, and to prevent upregulation of virulence genes in disease causing bacteria. Published literature has demonstrated that a cell or cells with lowered transmembrane potentials will signal disease causing bacteria to up regulate virulence genes and turn a benign bacteria into a virulent one. Viruses enter and exit cells by lowering the transmembrane potential. It has been shown that activation of some types of retro viruses which attach themselves to a hosts DNA will activate when the TMP is lowered. An example is that of the herpes simplex type I virus, which can cause fever blisters and shingles decades after someone has been initially infected (chicken pox). If the cell transmembrane potential is sufficiently high, the virus cannot lower the TMP enough to cause ingress or if the cell is infected with the virus, to allow replicated viri out of the cell. The device can be used to inhibit viral infection, prevent activation of latent viruses, and inhibit bacteria from up regulating virulence genes.

Oscillating fields cause forced vibrations of all free ions on the surface of a cells plasma membrane via coherence effects. The output of both the predicate and improved device is a oscillating pulse. The improved device having higher PRR than the predicate device is capable of creating the effect across a wider class of ions and creates stronger coherence effects due to increased wave amplitude formation. In this situation the coherence is created as a form of forced resonance.

When the output of the device is connected to an antenna or a device designed specifically to use RF energy such as an antenna, electrodes, a transducer or other RF emitter/antenna; the transmitter can be used to produce biophysiologic effects. These effects extend to all types of single and multicellular organisms, micro organisms, and cell types such as cancer. These effects can be detrimental or beneficial depending upon several parameters such as: modulation frequency, exposure time, field strength, and antenna emissions.

Gene Switching (up and down regulation) Published literature shows that specific genes may be up and down regulated based upon the applied frequency of an EM field. The improved device, providing a superior PRR to the predicate device offers the capability to influence a wider variety of genes than the predicate device.

Bioelectric X-Ray Effect—Published literature shows enhancement of the effects of therapeutic ionizing radiation especially in cancer from pulsed EM fields. EM field exposure following ionizing radiation exposure increases the effectiveness of the radiation on cancer cells. The improved device provides a superior PRR to that of the predicate device and can be utilized to provide a superior Bio Electric X-Ray effect.

BRIEF DESCRIPTION OF THE DRAWINGS

Additional objects and features of the present invention will be described in more detail with respect to the following Figures in which:

FIG. 3 is the output of the prior art device at 500 KHz with 50% duty cycle;

FIG. 4 is a diagram of the output of the present invention at 500 KHz at 50% duty cycle;

FIG. 5 is a block diagram of the present invention utilizing a balun;

FIG. 9 is a diagram of an internal electro glass plasma tube/antenna;

FIG. 10 illustrates a current balun;

FIG. 11 illustrates a voltage balun; and

DETAILED DESCRIPTION OF THE PRESENT INVENTION

Figure 6:
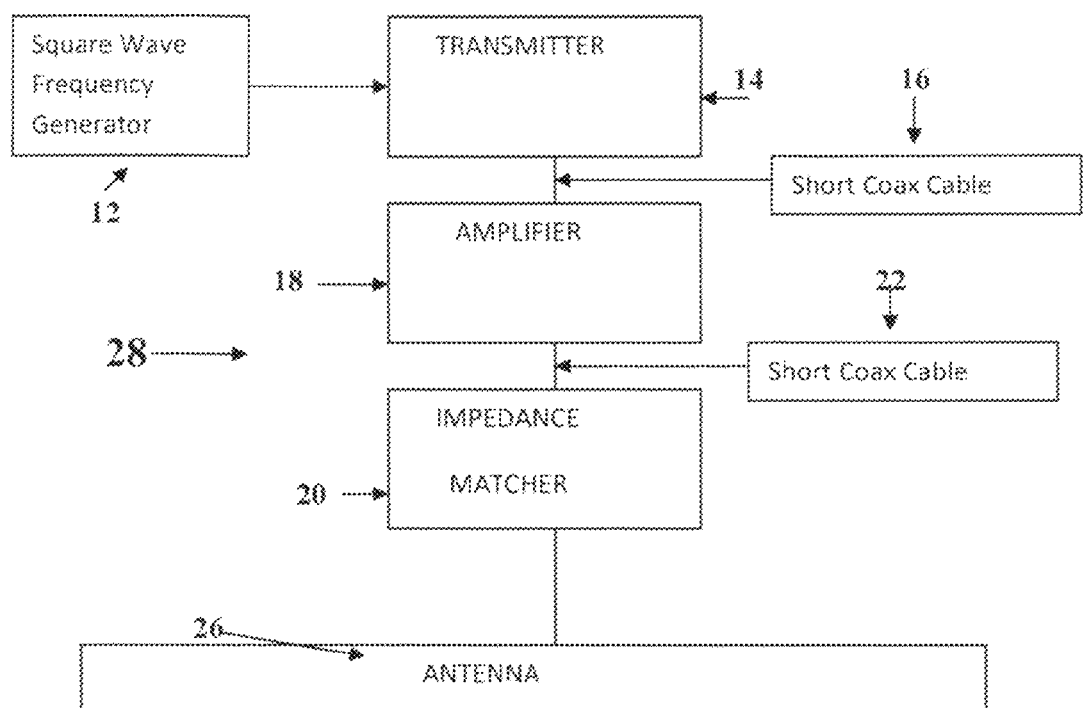
FIG. 6 is a block diagram of the present invention without the utilization of a balun.
Figure 2:
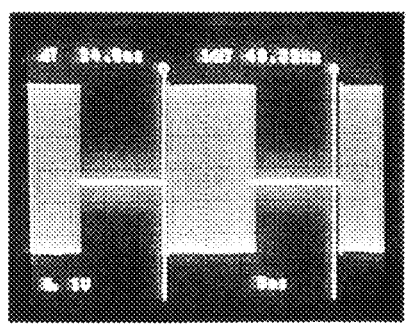
FIG. 2 is an output of the present invention at 40 Hz with 50% duty cycle.
Figure 1:
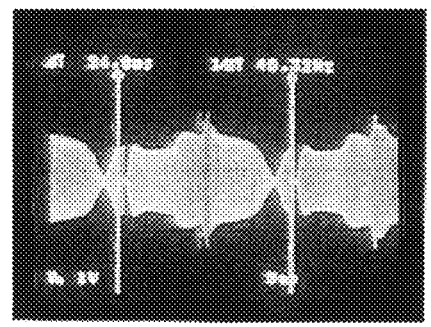
FIG. 1 is a diagram of the output of a prior art device at 40 Hz with 50% duty cycle.

FIGS. 5 and 6 illustrate the present invention utilizing a balun (FIG. 5) as well as without use of a balun (FIG. 6). Both of these figures will be described with the utilization of like reference numerals being assigned to the same device. A square wave generator 12, as shown in the circuit 10 of FIG. 5 and the circuit 28 of FIG. 6 will be connected to a transmitter 14 which is described in U.S. patent application Ser. No. 12/457,502, filed on Jun. 12, 2009, is incorporated by reference, and described with respect to FIGS. 12 and 13. The transmitter 14 will be connected to an amplifier 18 by a direct connection or by a short coaxial cable 16. The amplifier 18 will be connected to an impedance matching circuit 20 either directly or by a relatively short coaxial cable 22. The length of these coaxial cables should be less than one foot. The impedance matching circuit 20 is either directly connected to an antenna 26 or either by a voltage or current balun 24 provided between the impedance matching circuit 20 and the antenna 26. The impedance matching circuit is designed to be almost self-resonant utilizing an inductor coil and minimal adjustable capacitance. Relatively large sized surface tuning plates would work very well. A relatively small number of turning plates, preferably between 3 and 5, will be used. Even with the utilization of a balun 24, it has been found that the impendence matching circuit 20 should be provided as close to the antenna 26 as possible.

Figure 7:
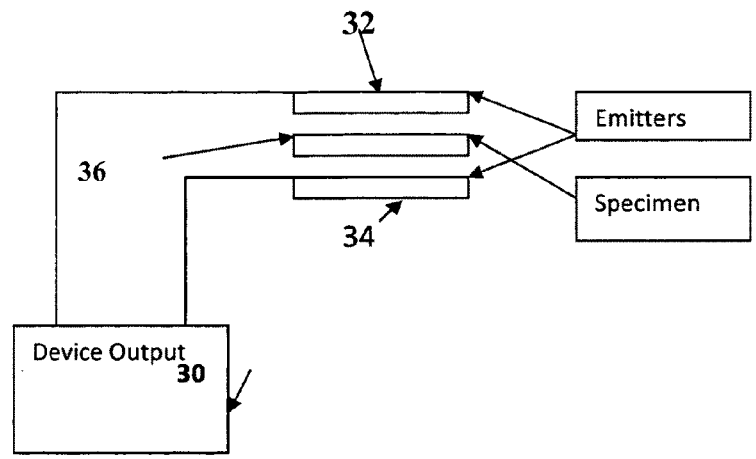
FIG. 7 is a block diagram of the present invention creating electro kinetic effects.

The present invention as illustrated with respect to FIGS. 5 and 6 can be applied to create electro kinetic effects as shown in FIG. 7. The device 30 represents the square wave frequency generator, transmitter, amplifier, impedance matcher and balun of FIG. 5 or the lack of the balun in FIG. 6. The device 30 is coupled to a pair of emitters 34 having a specimen 36 provided therebetween. The emitters 32 and 34 would be placed as close to the specimen 36 as possible to maximize the field strength and to produce the desired effects. These desired effects can be physically observed using direct physical observation or with the addition of a microscope, video camera or similar device.

Figure 8:
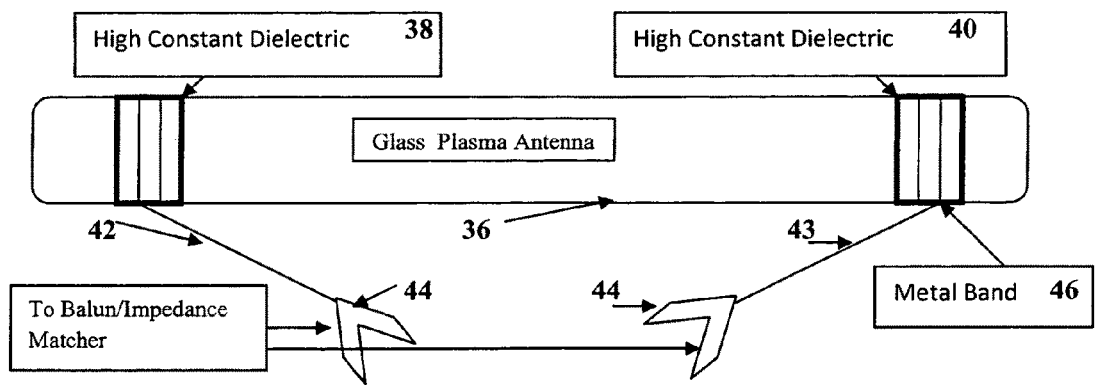
FIG. 8 is a diagram of the present invention using a tube capacitive coupling method.

FIG. 8 illustrates the use of a plasma tube as the antenna for the present invention. The antenna is capacitively connected to either the balun 24 shown in FIG. 5 or directly to the impedance matching circuit 20 shown in FIG. 6. Reference numerals 44 represent the balun or impedance matching circuit shown in FIGS. 5 and 6 connected to the metal band 46 by a direct conductor 43 or to the insulator 38 by conductor 42. Additionally, the high constant dielectric insulator 40 is connected to the metal band 46. It is noted that any type of conductive gas plasma can be provided within the glass plasma tube 36, with the tube glass also acting as an insulator. The insulator could be Teflon. This is accomplished by wrapping the plasma tube under the area of the conductor. It is noted that other dielectric material could be used as the insulator.

FIG. 9 illustrates two types of internal electrode tubes which may be utilized. It is noted that these tubes are a general representation of the tubes which can be employed. Typical tubes are shown by reference numerals 50 and 52. The internal electrode shape, size, arrangement and design may vary based upon the type of tube which is used. Tubes with internal electrodes are directly connected to the output of the balun or the impedance matcher and no dielectric insulation is used.

FIG. 10 illustrates a current balun 54 which is inserted between the output of the impedance matching circuit 20 and the antenna 26 shown in FIG. 5. The current balun 54 is connected at both ends to the ground and one end is connected to the impedance matching circuit 20 and the second end to the antenna 26 of FIG. 5. This current balun could be constructed from a plurality of ferrite beads. The hot lead from the tuner goes to the input side of the current balun and the output side of the current balun.

FIG. 11 shows a voltage balun 56 containing a plurality of wrapping wires 58. The hot lead from the tuner goes to the input side of the voltage balun which is also one of the output sides of the voltage balun.

Figure 12:
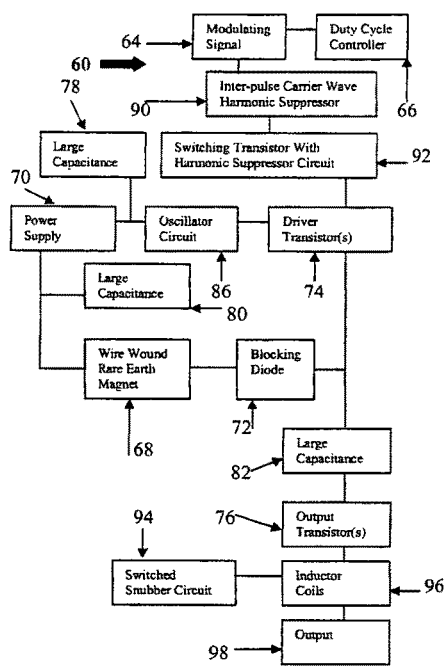
FIGS. 12 and 13 illustrate the embodiments of the transmitter used in the present invention.
Figure 13:
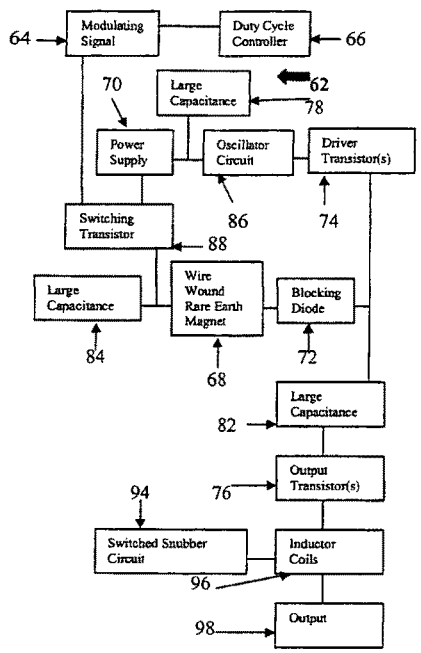

FIGS. 12 and 13 illustrate two embodiments of the amplitude modulated pulse transmitter, the similarities and the differences will be described herein below used with the present invention. As shown in these figures, a modulated signal 64 is introduced into the either of the transmitting circuits 60, 62. The duty cycle of this signal would be controlled by a standard duty cycle controller 66.

Both of the transmitters 60, 62 would utilize a wire wound rare earth magnet 68 instead of a transformer used in a standard AM modulated pulse transmitter. Typical of the rare earth magnets utilized in the present invention is a bar magnet having a wire wrapped therearound in a sequential manner. A ring magnet, similar to the bar magnet, including a wire wrap could be used. Each of the rare earth magnets would have a high gauss rating and is wound a number of times with their respective wires. It is preferable that these wires be made of solid copper to create a type of circular magnetic inductor. As shown in FIG. 6, the rare earth magnet 68 is directly connected between a standard power supply 70 and a blocking diode 72. This is the high power side of the transmitter circuit which would supply voltage and current to the collector's source (FET) of the driver transistor or transistors 74 as well as the output transistor or transistors 76.

It has been determined that the number of turns of the wire in either the bar magnet or the ring magnet would affect the operation of the transmitters 60, 62. For example, utilizing a ring magnet having a 0.75 inch diameter, a suitable range of turns would be between 15 and 25. Based upon the sizes and shapes (square, rectangular and so forth) the number of magnets, as well as the different sizes of wire, different circuits and different strengths of magnets will cause a variation in the number of necessary turns. Employing the high gauss rare earth magnets, many of the circuit's reactances are eliminated and the output power tends to stay very flat with increases in modulation frequencies. Output impedance stays very constant with only slight variations across a multi MHz wide modulation frequency range.

The pulse shaped, frequency response and irregularity of each carrier oscillation in the pulse is corrected by stabilizing the pulse shape at high frequencies. This is accomplished utilizing the large capacitors 78, 80 and 82 of FIG. 6 as well as the large capacitors 78, 80 and 84 of the circuit illustrated with respect to FIG. 13. It has been found that electrolytic capacitors having a range of 3300 uf to approximately 10,000 uf are added to improve the pulse shape and frequency response. The capacitor 78 in both circuits is provided in parallel to the low voltage input 70 of the power supply that powers an oscillator circuit 86. A second large electrolytic capacitor 30 having the same parameters of the capacitor 78 is provided in parallel to the high voltage input side of the circuit between the power supply 70 and the rare earth magnet 68. The large capacitor 84 of FIG. 13 is provided between the power supply 70 and the rare earth magnet 68 through a switching transistor 88. In this second embodiment, the modulated signal is directly connected to the switching transistor 88. A third large electrolytic capacitor 82 having the same parameters as the first and second large capacitors is added in series to the circuit that feeds the collector (FET source) of the driver transistor or transistors 74 and the base (FET-Gate) of the output transistor or transistors 76 in both FIGS. 6 and 7.

It is important to note that the large capacitor 82 is installed backwards with the negative side of the capacitor receiving positive power from the high voltage side of the circuit that feeds the collectors of the output transistor or transistors 76. The positive side of this capacitor is attached to the collector or collectors of the drive transistor or transistors 74 and to the base of the output transistor or transistors. Installing this capacitor 82 backwards decreases the rise and fall time of the pulse envelope. Additionally, the voltage rating of the capacitor must be significantly higher than that of the voltage entering it. It is important to note that use of a non-polar electrolytic capacitor in this position results in a slight degradation of rise and fall time pulse envelope shaping and modulation frequency capability can be employed. Use of these high value capacitors will improve the pulse shape; assist in stabilizing output power level of the transmitter and increase pulse frequency bandwidth. The capacitor 82 must have a significantly higher voltage rating than would normally be used in this type of transmitter. For example, a 30 volt capacitor might be used if installed normally. In this case, a 100 volt rating or more must be used. If a non polar electrolytic capacitor is used, the voltage of the capacitor can be set for the circuit (30 volts).

Prior art high level AM modulated pulse transmitters would use a modulation transformer. In this case, a blocking diode was used to prevent ingress of RF energy into the modulation transformers. Both of the circuits shown in FIGS. 12 and 13 would use a similar blocking diode 72 to limit RF entry back to the power supply after passing through the rare earth magnets 32. This blocking diode plays an important role in the modulation pass band and impedance stabilization ability of the transmitter. The diode 72 is connected to the source of the driver transistors 74 and the output transistors 76 and the electrical parameters of the diode are important to the operation of the transmitter. An incorrect diode would cause a limit of the pass band, a degradation of the pulse shape, a limit to the duty cycle response at high KHz and MHz frequencies, as well as slow rise and fall time. The blocking diode 72 would have a low forward resistance which can effect the RC time which can affect the pass band and pulse shape, the circuit reactance which affect the pass band as well as the circuit reactance which effect the transmitter output impedance variation with modulation frequency. The RC as well as LC time constants are calculated utilizing the following:

The RC time constant is identified by the Greek letter τ. The time constant is given in seconds.

τ=R×C Where R is the circuit resistance in ohms and C is the circuit capacitance in farads.

The cutoff frequency or $f_c$ is the maximum frequency a circuit will pass and is related to τ. Cutoff frequency is calculated in this manner.

$$\tau = RC = \frac{1}{2\pi f_c}$$

or $$f_c = \frac{1}{2\pi RC} = \frac{1}{2\pi \tau}$$

The LC time constant is derived by the formula

Time=L/R Where L is inductance in Henry's and R is the resistance in Ohms and Time is in seconds.

The cutoff frequency is the maximum frequency the circuit will pass, and what is wanted is a high cut off frequency. At MHz pulse rates times get very short—billionths of a second. As can be seen, it is the combined values of R, C, or L, which can increase, or if one is not careful, decrease the cut off frequency. In this transmitter—one must be careful of how the values are combined. What is wanted are very high MHz cut off frequencies. The transmitter is capable of generating pulses of 100 nanosecond or 100 billionths of a second duration. This all applies to the blocking diode. Diodes have voltage losses across them due to internal resistances, as well as on/off switching time, which both play a part in the transmitters pulse rate capability.

Increasing voltage of the low voltage side of the circuit which includes the oscillator, to a value approximately 50 to 60% of the high voltage side of the circuit decreases the rise and fall time of the pulse, increases output power across the transmitters pulse bandwidth, improves pulse envelope shape, and decreases ringing of the pulse. For example the high voltage side of the circuit that feeds the collectors (FET-Source) of the output transistors may be operating at 31 volts, while the low voltage side of the circuit would be operated at 16 volts.

Increasing the current to the low voltage side of the circuit, which includes the oscillator, while holding the voltage at a low level (13 Volts typical) will produce an effect similar to that of increasing the voltage. That is, an increase in current will increase output power across the transmitter bandwidth, improve pulse envelope shape, and decrease ringing of the pulse. The advantage of increasing current over increasing voltage of the low voltage—oscillator side of the circuit, is that when using an amplifier with a high conduction angle, the carrier wave will not fully cut off between pulses, and the carrier will tend to be of significant enough power between pulses to damage an amplifiers transistors. As such, a low voltage with high current improves the ability of the transmitter to be used with an amplifier.

Circuit ringing between pulses can become evident at modulation frequencies of 1 MHz and above. This is important since the range of the transmitter of the present invention can be as great as 4 MHz and above. If severe enough, the circuit ringing can cause limitation of the pulse bandwidth capability. One manner in which this situation can be alleviated would be to utilize a harmonic suppressor 90 with a switching transistor 92 in the first embodiment illustrated with respect to FIG. 12. The switching transistor 92 is utilized with a resistor and a diode. The resistor is approximately 12 ohms and one end is connected to the base of the switching transistor 62. The other end of the resistor is attached to the anode of the diode. The cathode of the diode is connected to the collector of the switching transistor.

Another manner of controlling the circuit ringing is to use a switched snubber circuit 94 as illustrated in FIG. 12. The snubber circuit can be used with both the transmitters shown in FIGS. 6 and 7. This circuit includes a resistor and capacitor provided in series with one end of the capacitor attached to ground. The resistor and capacitor are connected in series to a tuning inductor coil 96. The coil 96 or coils are provided between the output transistor 76 and an output jack 98. Additionally, switch 74 is provided between the coils 42 and the snubber circuit 40.

The circuit illustrated in FIG. 12 also includes an inter-pulse carrier wave harmonic suppressor 90. This circuit would eliminate the inter-pulse carrier wave harmonic form by utilizing a small resistor and an electrolytic capacitor between the modulation signal input jack and the switching transistor. The small resistor could be of approximately 50 ohms and the electrolytic capacitor would be about 20 uf placed in parallel to each other and in series with the input modulation signal before the signal is sent to the base of the switching transistor. The positive end of the electrolytic capacitor is attached to the input side of the wave signal. The use of this arrangement would eliminate damage to power transistors that would be used in an attached amplifier.

The foregoing description of the preferred embodiment of the invention has been presented for purposes of illustration and description. It is not intended to be exhausted or to limit the invention to the precise form disclosed, and obviously many modifications and variations are possible in light of the above teaching. The proceeding embodiments which show and describe in order to best explain the principles invention and its practical application to thereby enable others skilled in the art to best utilize the invention in the described embodiments and with various modifications as are suited to the particular use contemplated.

What is claimed is:

1. A resonant frequency device comprising:
   an amplitude modulated pulse transmitter comprising:
      a modulated signal producing device providing a modulating signal;
      at least one driver transistor;
      an oscillator circuit connected to said at least one. driver transistor;
      a power supply having a high voltage side connected to said oscillator circuit;
      a wire wound rare earth magnet connected to said power supply and said modulated signal producing device;
      at least one output transistor in communication with said wire wound rare earth magnet and said at least one driver transistor;
      an output jack in communication with said at least one output transistor, wherein the amplitude modulated pulse transmitter provides a modulated pulse output in the range of between 7000 Hz and 4 MHz without the utilization of a transformer;
   a square wave generator generating square waves having rise and fall times less than 40 nanoseconds, said square wave generator connected to said amplitude modulated pulse transmitter;
   an amplifier in communication with said transmitter;
   an impedance matching circuit in communication with said amplifier;
   an antenna in communication with said impedance matching circuit, said antenna being a glass plasma tube having a gas therein; and
   a Teflon insulator provided proximate to each end of said antenna.

2. The resonant frequency device in accordance with claim 1, further including a balun provided between said impedance matching circuit and said antenna.

3. The resonant frequency device in accordance with claim 2, wherein said balun is a currant balun.

4. The resonant frequency device in accordance with claim 2, wherein said balun is a voltage balun.

5. The resonant frequency device in accordance with claim 2, wherein said impedance matching circuit includes between three and five large surface tuning plates.

6. The resonant frequency device in accordance with claim 2, further including first and second conductors provided between said balun and said antenna, said Teflon insulator wrapped around each of said first and second conductors.

7. The resonant frequency device in accordance with claim 1, wherein said gas is helium.

8. The resonant frequency device in accordance with claim 1, wherein said impedance matching circuit includes between three and five large surface tuning plates.

* * * * *

UNITED STATES PATENT AND TRADEMARK OFFICE
CERTIFICATE OF CORRECTION

| | |
|---|---|
| PATENT NO. | : 8,652,184 B2 |
| APPLICATION NO. | : 12/461706 |
| DATED | : February 18, 2014 |
| INVENTOR(S) | : James E. Bare |

It is certified that error appears in the above-identified patent and that said Letters Patent is hereby corrected as shown below:

In The Claims

Column 18, line 14, cancel the text beginning with "1. A resonant frequency" to and ending "of said antenna", and insert the following claim:

--1. A resonant frequency device comprising:
   an amplitude modulated pulse transmitter comprising:
   a modulated signal producing device providing a modulating signal;
   at least one driver transistor;
   an oscillator circuit connected to said at least one driver transistor;
   a power supply having a high voltage side connected to said oscillator circuit;
   a wire wound rare earth magnet connected to said power supply and said modulated signal producing device;
   at least one output transistor in communication with said wire wound rare earth magnet and said at least one driver transistor;
   an output jack in communication with said at least one output transistor, wherein the amplitude modulated pulse transmitter provides a modulated pulse output in the range of between 7000 Hz and 4 MHz without the utilization of a transformer;
   a square wave generator generating square waves having rise and fall times less than 40 nanoseconds, said square wave generator connected to said amplitude modulated pulse transmitter;
   an amplifier in communication with said transmitter;
   an impedance matching circuit in communication with said amplifier;
   an antenna in communication with said impedance matching circuit, said antenna being a glass plasma tube having a gas therein; and
   a Teflon insulator provided proximate to each end of said antenna.--

Signed and Sealed this
Ninth Day of December, 2014

Michelle K. Lee
*Deputy Director of the United States Patent and Trademark Office*

CERTIFICATE OF CORRECTION (continued)
U.S. Pat. No. 8,652,184 B2

Column 18, line 48, cancel the text beginning with "3. The resonant frequency" to and ending "a currant balun", and insert the following claim:

--3. The resonant frequency device in accordance with claim 2, wherein said balun is a current balun.--